United States Patent
Zhang

(10) Patent No.: US 11,331,195 B2
(45) Date of Patent: May 17, 2022

(54) ARTICULAR GASKET PROSTHESIS AND ARTICULAR PROSTHESIS WITH ARTICULAR GASKET PROSTHESIS

(71) Applicant: Beijing AK Medical Co., Ltd., Beijing (CN)

(72) Inventor: Weiping Zhang, Beijing (CN)

(73) Assignee: Beijing AK Medical Co., Ltd., Beijing (CN)

( * ) Notice: Subject to any disclaimer, the term of this patent is extended or adjusted under 35 U.S.C. 154(b) by 0 days.

(21) Appl. No.: 17/042,962

(22) PCT Filed: Apr. 4, 2019

(86) PCT No.: PCT/CN2019/081498
§ 371 (c)(1),
(2) Date: Sep. 29, 2020

(87) PCT Pub. No.: WO2020/155378
PCT Pub. Date: Aug. 6, 2020

(65) Prior Publication Data
US 2021/0353423 A1 Nov. 18, 2021

(30) Foreign Application Priority Data
Feb. 1, 2019 (CN) .......................... 201910105642.0

(51) Int. Cl.
*A61F 2/38* (2006.01)
*A61F 2/30* (2006.01)

(52) U.S. Cl.
CPC ........ *A61F 2/3877* (2013.01); *A61F 2/30771* (2013.01); *A61F 2002/30014* (2013.01);
(Continued)

(58) Field of Classification Search
CPC ...................................... A61F 2/389
See application file for complete search history.

(56) References Cited

U.S. PATENT DOCUMENTS 5,549,700 A * 8/1996 Graham ................ A61F 2/3609
623/22.14
5,766,256 A * 6/1998 Oudard .................. A61F 2/389
623/20.32
(Continued)

FOREIGN PATENT DOCUMENTS

| CN | 1671333 A | 9/2005 |
| CN | 105813605 A | 7/2016 |
| CN | 105816259 A | 8/2016 |

OTHER PUBLICATIONS

The extended European search report of the corresponding EP patent application No. 19914127.6, dated Nov. 19, 2021.

*Primary Examiner* — Yashita Sharma
*Assistant Examiner* — Melissa A Hoban
(74) *Attorney, Agent, or Firm* — Gang Yu

(57) ABSTRACT

The disclosure provides an articular gasket prosthesis and an articular prosthesis with the articular gasket prosthesis. The articular gasket prosthesis includes an elastic gasket disposed between a first skeleton and second skeleton forming a joint, the elastic gasket including: an elastic matrix, having a first contact surface facing the first skeleton and a second contact surface facing the second skeleton; and multiple synovial fluid passages, distributed in the elastic matrix and communicating the first contact surface and the second contact surface, the multiple synovial fluid passages being disposed according to a predetermined manner to gradually increase hardness of the elastic matrix from a center to an edge and gradually decrease elasticity of the elastic matrix from the center to the edge.

18 Claims, 8 Drawing Sheets

(52) U.S. Cl.
CPC ............... *A61F 2002/30518* (2013.01); *A61F 2002/30563* (2013.01); *A61F 2002/30772* (2013.01); *A61F 2002/30827* (2013.01); *A61F 2002/3881* (2013.01); *A61F 2002/3895* (2013.01)

(56) References Cited

U.S. PATENT DOCUMENTS

| | | | | |
|---|---|---|---|---|
| 5,916,269 | A * | 6/1999 | Serbousek | A61F 2/34 623/22.24 |
| 7,124,067 | B2 * | 10/2006 | Ascenzi | B33Y 50/00 703/11 |
| 7,396,505 | B2 * | 7/2008 | Pope | B22F 7/062 419/9 |
| 8,350,186 | B2 * | 1/2013 | Jones | B22F 10/20 219/121.66 |
| 8,979,938 | B2 * | 3/2015 | Linares | A61F 2/38 623/22.15 |
| 2003/0014122 | A1 * | 1/2003 | Whiteside | A61F 2/389 623/20.32 |
| 2003/0114936 | A1 * | 6/2003 | Sherwood | A61F 2/30942 623/23.58 |
| 2004/0062786 | A1 * | 4/2004 | Ascenzi | G09B 23/30 424/423 |
| 2005/0055101 | A1 | 3/2005 | Sifneos | |
| 2005/0112397 | A1 * | 5/2005 | Rolfe | A61F 2/0811 428/593 |
| 2005/0202371 | A1 | 9/2005 | McGuire | |
| 2006/0241767 | A1 * | 10/2006 | Doty | A61F 2/4425 623/17.12 |
| 2006/0276900 | A1 | 12/2006 | Carpenter | |
| 2007/0100450 | A1 | 5/2007 | Hodorek | |
| 2007/0179613 | A1 | 8/2007 | Heinz | |
| 2008/0147191 | A1 | 6/2008 | Lopez et al. | |
| 2009/0234453 | A1 | 9/2009 | Steinberg | |
| 2010/0331998 | A1 * | 12/2010 | Ringeisen | A61L 27/50 623/23.61 |
| 2011/0118845 | A1 | 5/2011 | Overes et al. | |
| 2013/0150977 | A1 * | 6/2013 | Gabriel | A61F 2/389 623/20.32 |
| 2015/0238317 | A1 | 8/2015 | Bonutti | |
| 2018/0289493 | A1 * | 10/2018 | Mansmann | A61F 2/30756 |
| 2018/0318106 | A1 | 11/2018 | Ball | |
| 2019/0053915 | A1 * | 2/2019 | Macke | A61F 2/34 |
| 2021/0069409 | A1 * | 3/2021 | Castleberry | A61M 5/14212 |

\* cited by examiner

ARTICULAR GASKET PROSTHESIS AND ARTICULAR PROSTHESIS WITH ARTICULAR GASKET PROSTHESIS

CROSS-REFERENCE TO RELATED APPLICATION(S)

The present application claims priority to Chinese Patent Application No. 201910105642.0, filed on Feb. 1, 2019 and entitled "Articular Gasket Prosthesis and Articular Prosthesis with Articular Gasket Prosthesis", the contents of which are hereby incorporated by reference in its entirety.

TECHNICAL FIELD

The disclosure relates to a field of artificial prosthesis replacement, and particularly to an articular gasket prosthesis and an articular prosthesis with the articular gasket prosthesis.

BACKGROUND

In a present knee joint prosthesis for an artificial knee joint replacement operation, a femoral condyle prosthesis is usually made from a medical metal, for example, stainless steel or a cobalt alloy, on a tibia side, and a gasket is made from ultra-high molecular weight polyethylene on a tibia side. For a kinematic requirement of a knee joint, a metal articular surface of the femoral condyle prosthesis is usually designed into a complex continuous spatial curved surface, but the ultra-high molecular weight polyethylene articular surface gasket on the tibia side may only be designed into a curved surface with a relatively high matching degree with the articular surface on the femur side according to a specific position (for example, an upright position), to ensure stability in an upright state. However, along with motions of the knee joint, a contact area between the femoral condyle prosthesis and the articular surface gasket may be far smaller than an ideal value, which causes excessively high pressure between the femoral condyle prosthesis and the articular surface gasket and accelerates wear to the articular surface gasket. In addition, since no close connections may be established between ligaments and tissues around the operated joint and the implanted artificial articular prosthesis like those between original articular biological tissues, stability of a mechanical system, of which balance heavily depends on soft tissues, of the knee joint is greatly reduced.

SUMMARY

The disclosure is intended to provide an articular gasket prosthesis and an articular prosthesis with the articular gasket prosthesis, to solve the problem of short service life of an articular prosthesis of a patient caused by excessively high local pressure and serious wear of an articular gasket prosthesis due to the fact that a contact area between a femoral condyle prosthesis and the articular gasket prosthesis may not be ensured in a conventional art.

To this end, according to one aspect of the disclosure, an articular gasket prosthesis is provided, which includes an elastic gasket disposed between a first skeleton and a second skeleton, wherein the first skeleton and the second skeleton form a joint, the first skeleton referring to a skeleton forming a significant sliding friction relationship with the articular gasket prosthesis of the disclosure and the second skeleton referring to a skeleton on which the articular gasket prosthesis of the disclosure is fixed, wherein the elastic gasket includes: an elastic matrix, having a first contact surface facing the first skeleton and a second contact surface facing the second skeleton; and a plurality of synovial fluid passages, distributed in the elastic matrix and communicating the first contact surface and the second contact surface, the plurality of synovial fluid passages being disposed according to a predetermined manner, so as to gradually increase a hardness of the elastic matrix from a center to an edge and gradually decrease an elasticity of the elastic matrix from the center to the edge.

In some embodiments, the plurality of synovial fluid passages include a plurality of accommodation cavity layers and a plurality of flow passages, the plurality of accommodation cavity layers are disposed in a direction from the first contact surface to the second contact surface, each of the plurality of accommodation cavity layers includes a plurality of accommodation cavities, and each of the plurality of flow passages is connected between two adjacent accommodation cavity layers of the plurality of accommodation cavity layers.

In some embodiments, volumes of the plurality of accommodation cavity layers are gradually decreased in the direction from the first contact surface to the second contact surface.

In some embodiments, the plurality of accommodation cavities are gradually reduced in the direction from the first contact surface to the second contact surface.

In some embodiments, volumes of the plurality of accommodation cavities in a same accommodation cavity layer are gradually decreased from a center to an edge of the same accommodation cavity layer.

In some embodiments, the synovial fluid passages further include an inflow passage, and a check valve is disposed in the inflow passage, the inflow passage is communicated with at least one accommodation cavity of the plurality of accommodation cavities, or the inflow passage is communicated with at least one flow passage of the plurality of flow passages, or the inflow passage is communicated with at least one accommodation cavity of the plurality of accommodation cavities and at least one flow passage of the plurality of flow passages.

In some embodiments, the articular gasket prosthesis further includes a gasket matrix, the gasket matrix is disposed between the first skeleton and the second skeleton, the gasket matrix is provided with an accommodation groove, the elastic gasket is disposed in the accommodation groove, and a hardness of the gasket matrix is higher than a hardness of the elastic gasket.

In some embodiments, a positioning protruding portion is disposed on a circumferential sidewall of the elastic matrix, and a positioning groove is formed at the position, corresponding to the positioning protruding portion, of the accommodation groove.

In some embodiments, a flow groove is formed in a bottom surface of the gasket matrix, and a communicating hole is formed in a bottom of the accommodation groove and communicated with the flow groove such that a synovial fluid is able to enter the accommodation groove through the flow groove and the communicating hole.

In some embodiments, the gasket matrix further includes a communicating passage, an inlet of the communicating passage extends onto a top surface of the gasket matrix, and an outlet of the communicating passage is communicated with the inflow passage.

In some embodiments, the articular gasket prosthesis further includes a reinforcing ring, and the reinforcing ring is disposed on a circumferential outer side of the gasket matrix.

In some embodiments, both of a penetration layer and integration layer of the reinforcing ring are of a porous structure, the penetration layer is able to form contact fusion with the gasket matrix, soft tissues around the joint are able to grow into the integration layer, and an isolation layer is disposed between the penetration layer and the integration layer.

In some embodiments, both of the penetration layer and integration layer of the reinforcing ring are of a porous structure, a pore diameter of the porous structure of the penetration layer is 500 μm to 3,000 μm, and a pore diameter of the porous structure of the integration layer is 400 μm to 2,000 μm.

In some embodiments, the elastic gasket is made from an elastic transparent polymer material or composite material.

According to the other aspect of the disclosure, an articular prosthesis is provided, which includes the articular gasket prosthesis being the abovementioned articular gasket prosthesis.

In some embodiments, the articular prosthesis is a knee joint prosthesis, and the knee joint prosthesis further includes a tibial plateau prosthesis and a femoral condyle prosthesis.

With application of the technical solutions of the disclosure, the synovial fluid passages are disposed in the elastic gasket according to the predetermined manner, and parameters such as sectional shapes, pore diameters, lengths, volumes, positions, arrangement direction and density of the synovial fluid passages are regulated to gradually increase the hardness of the elastic matrix from the center to the edge and also gradually decrease the elasticity from the center to the edge, so that different elasticity and hardness indexes may be achieved at different predetermined parts of the elastic gasket to make the elastic gasket close to mechanical characteristics of a human joint as much as possible, the elastic gasket may fully contact with an articular skeleton during joint motions, pressure between contact surfaces is further kept within an ideal range, and a using effect and service life of the articular gasket prosthesis are ensured. In addition, such a porous structure design that the pore aperture of the integration layer of the reinforcing ring is 400 μm to 2,000 μm enables soft tissues such as an articular capsule and primary ligament residues wrapping the articular gasket prosthesis after an operation to grow in pores of the porous structure of the integration layer to form biological tissue integration and enables the soft tissues such as ligaments to grow in the pores of the porous structure in a postoperative healing process, so that a postoperative knee joint system is more stable.

BRIEF DESCRIPTION OF THE DRAWINGS

The drawings forming a part of the application in the specification are adopted to provide a further understanding to the disclosure. Schematic embodiments of the disclosure and descriptions thereof are adopted to explain the disclosure and not intended to form improper limits to the disclosure. In the drawings.

Figure 1:
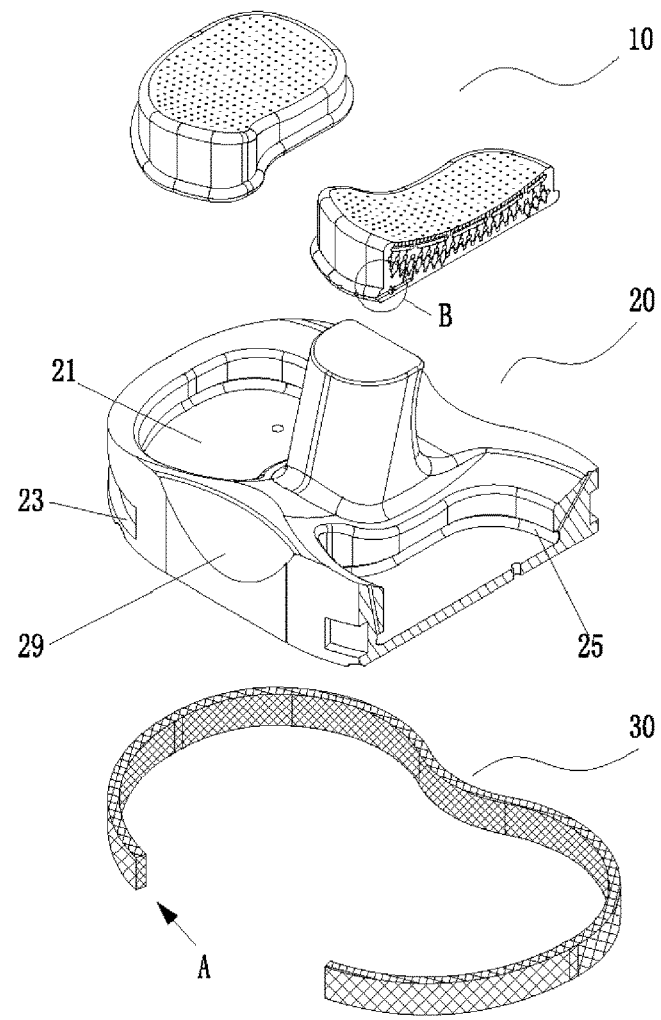
FIG. 1 is an exploded view of an articular gasket prosthesis according to embodiment 1 of the disclosure.

Herein, the drawings include the following drawing reference signs:

1: femoral condyle prosthesis; 2: articular gasket prosthesis; 3: tibial plateau prosthesis; 4: femoral condyle; 5: patella structure; 10: elastic gasket; 11: accommodation cavity; 11*a*: accommodation cavity; 11*b*: accommodation cavity; 11*c*: accommodation cavity; 12: flow passage; 12*b*: flow passage; 12*c*: flow passage; 12*d*: flow passage; 13: inflow passage; 14: check valve; 15: positioning protruding portion; 20: gasket matrix; 21: accommodation groove; 23: reinforcing ring accommodation groove; 25: positioning groove; 26: flow groove; 27: communicating hole; 28: communicating passage; 29: patellar slot; 30: reinforcing ring; 31: integration layer; 32: isolation layer; and 33: penetration layer.

DETAILED DESCRIPTION OF THE EMBODIMENTS

An articular gasket prosthesis of the application is applied to artificial joint replacement operations and configured to absorb impacts generated by joint motions and reduce frictional damage between articular skeletons. For example, in a human knee joint, a femur swings and rotates relative to a tibia to implement leg bending and turning, and cartilages on a distal femur (femoral condyle) and a proximal tibia (tibial plateau) and meniscus structure act as a gasket between the femur and the tibia. Bending trends of upper and lower surfaces of the meniscus structure are approximate to those of a curved surface of the distal femur and a curved surface of the proximal tibia, a contact area of the joint is enlarged, stability of the joint is improved, and pressure is reduced. Meanwhile, the meniscus structure also has high elasticity and may be properly deformed to absorb impacts and shocks and adapted to an anatomic form of the distal femur when the knee joint moves to ensure coordination of a geometric form of the knee joint, thereby maintaining motion coordination of the knee joint.

In a present knee joint prosthesis for an artificial knee joint replacement operation, a femoral condyle prosthesis is usually made from a medical metal on a femur side, and a gasket is made from ultra-high molecular weight polyethylene on a tibia side. The gasket is undiversified in material and structure and, although having certain elasticity, may even recover a deformation amplitude and buffering and wear reduction effects of a primary meniscus structure and cartilage. In addition, since the gasket made from the ultra-high molecular weight polyethylene is not elastic enough, when the knee joint starts bending for motion, an effective contact area between the femoral condyle prosthesis and the gasket may be very small along with position and angle changes between the femur and the tibia, even only linear contact or point contact may be met at some positions, and local high pressure is generated at these positions to accelerate wear of an articular surface to further affect service life of the whole knee joint as well as the life of a patient after the operation. Moreover, there are no more close connections between ligaments and soft tissues around the primary joint and the implanted artificial joint prosthesis after the operation, stability of a mechanical system, of which balance heavily depends on the soft tissues, of the knee joint is greatly reduced. For the foregoing problems, the application discloses structural improvements in the gasket.

It is to be noted that the embodiments in the application and characteristics in the embodiments may be combined without conflicts. The disclosure will be described below with a knee joint as an example with reference to the drawings and in combination with the embodiments in detail.

Figure 2:
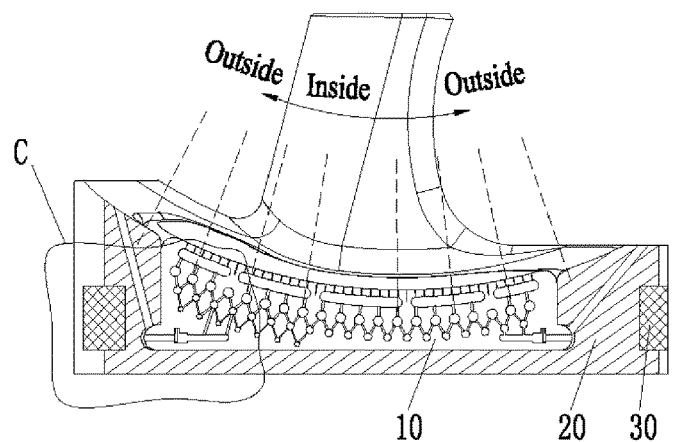
FIG. 2 is a section view of the articular gasket prosthesis in FIG. 1 in a combined state.
Figure 8:
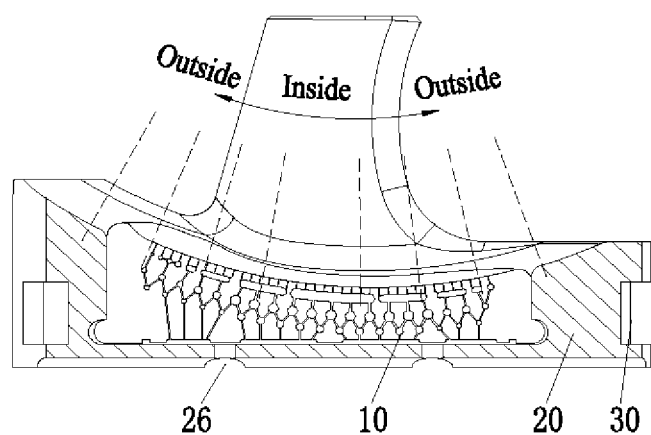
FIG. 8 is an exploded view of an articular gasket prosthesis according to embodiment 2 of the disclosure.

As shown in FIG. 1, FIG. 2 and FIG. 8, each of an articular gasket prosthesis of embodiment 1 and an articular gasket prosthesis of embodiment 2 includes an elastic gasket 10, the elastic gasket 10 is disposed between a femur structure and a tibia structure, and the elastic gasket 10 includes an elastic matrix and multiple synovial fluid passages distributed in the elastic matrix. The elastic matrix has a first contact surface facing the femur structure and a second contact surface facing the tibia structure, and the multiple synovial fluid passages communicate the first contact surface and the second contact surface to enable a synovial fluid to pass through the elastic matrix and flow in the elastic matrix. The multiple synovial fluid passages are disposed according to a predetermined manner to gradually increase a hardness of the elastic matrix from a center to an edge and gradually decrease elasticity of the elastic matrix from the center to the edge.

Figure 9:
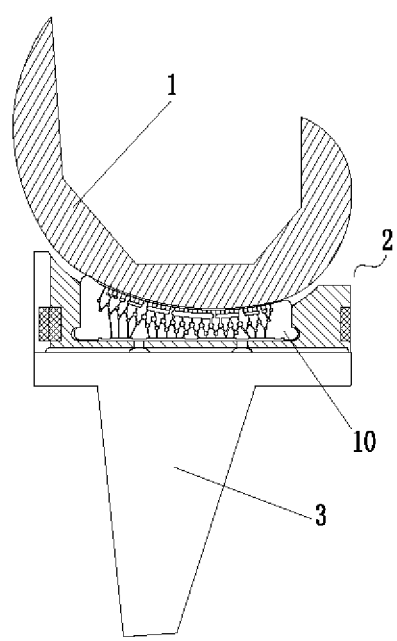
FIG. 9 to FIG. 11 are structure diagrams of the articular gasket prosthesis in FIG. 8 in different postures.
Figure 10:
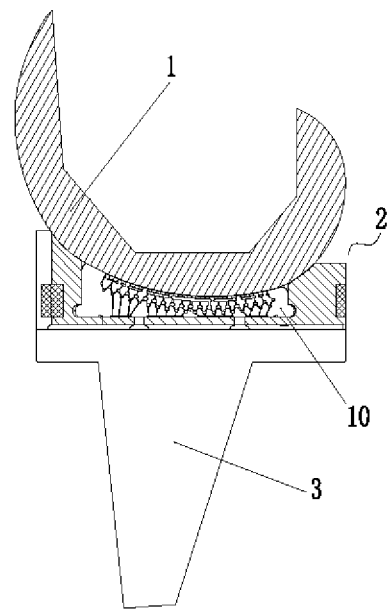
Figure 11:
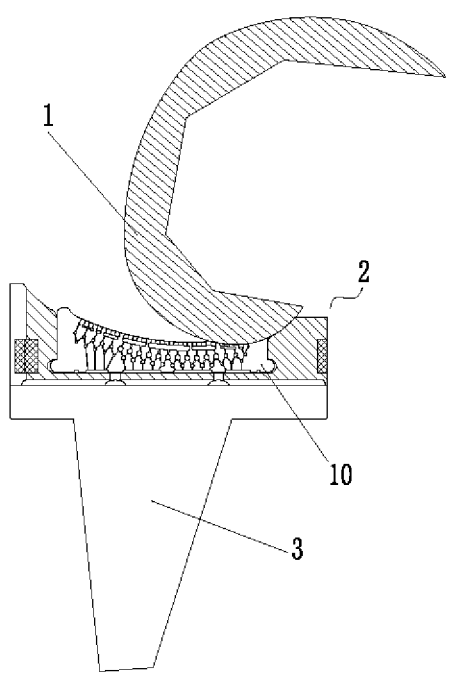
Figure 12:
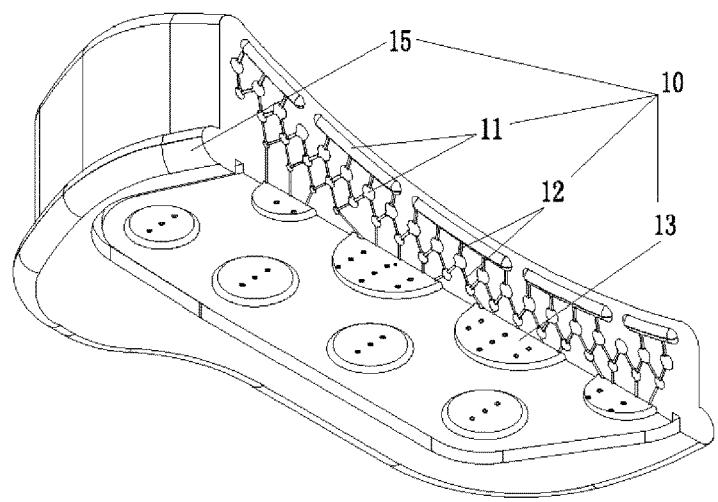
FIG. 12 is a section view of an elastic gasket of the articular gasket prosthesis in FIG. 8.

As shown in FIG. 9, in an unloaded and straightened state of a knee, the articular gasket prosthesis 2 is disposed on a tibial plateau prosthesis 3, and an upper surface of the elastic gasket 10 of the articular gasket prosthesis 2 is attached to a femoral condyle prosthesis 1. As shown in FIG. 10, a weight of a human body and an impact force are applied to the elastic gasket 10 of the articular gasket prosthesis 2, the elastic gasket 10 is compressed and deformed to achieve a buffer action, and in such case, a gasket matrix 20 and the elastic gasket 10 bear a mechanical load transmitted by the femoral condyle prosthesis together. As shown in FIG. 11, in a bent state of the knee joint, the elastic gasket 10 is locally compressed and deformed, and in such case, the elastic gasket may ensure a relatively enough contact area with the femoral condyle even under a non-uniform load and bear the mechanical load transmitted by the femoral condyle prosthesis together with the matrix 20 because of the characteristic that an outer side is relatively high in hardness and low in elasticity and an inner side is high in elasticity and low in hardness.

With application of the technical solution of the embodiment, the synovial fluid passages are disposed in the elastic gasket 10 according to the predetermined manner, and parameters such as sectional shapes, pore diameters, lengths, volumes, positions, arrangement direction and density of the synovial fluid passages are regulated to gradually increase the hardness of the elastic matrix from the center to the edge and gradually decrease the elasticity from the center to the edge, so that different elasticity and hardness indexes may be achieved at different predetermined parts of the elastic gasket 10 to make the elastic gasket 10 close to mechanical characteristics of a human knee joint as much as possible, the elastic gasket 10 may fully contact with the femoral condyle during knee joint motions, pressure between contact surfaces is further kept within an ideal range, and a using effect and service life of the articular gasket prosthesis are ensured.

Figure 3:
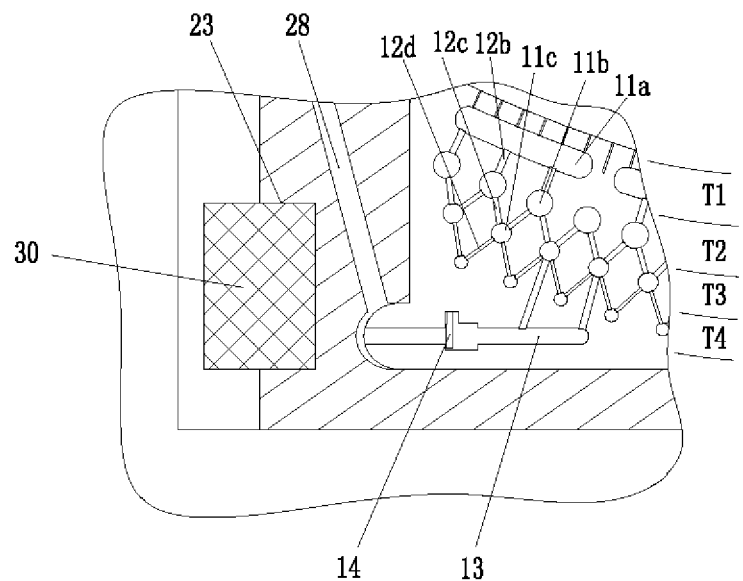
FIG. 3 is a partial enlarged view of the articular gasket prosthesis in FIG. 2 at C.

Preferably, in the embodiment, the elastic gasket 10 is made from an elastic transparent polymer material or composite material. As shown in FIG. 2 and FIG. 3, in the elastic gasket 10 of embodiment 1, the synovial fluid passages include multiple accommodation cavity layers (T1, T2, T3 and T4) and multiple flow passages 12, the accommodation cavity layer T1 to the accommodation cavity layer T4 are disposed in a direction from the first contact surface to the second contact surface, each accommodation cavity layer includes multiple accommodation cavities 11, and the flow passages 12 are connected between the accommodation cavities of two adjacent accommodation cavity layers. For example, the flow passage 12b communicates the accommodation cavity 11a of the accommodation cavity layer T1 and the accommodation cavity 11b of the accommodation cavity layer T2, the flow passage 12c communicates the accommodation cavity 11b and the accommodation cavity 11c of the accommodation cavity layer T3, and the flow passage 12d communicates the accommodation cavity 11c and the accommodation cavity of the accommodation cavity layer T4.

Specifically, as shown in FIG. 3, the multiple accommodation cavities 11 in the embodiment are gradually reduced from the accommodation cavity layer T1 to the accommodation cavity layer T4, and overall volumes of each accommodation cavity layer are gradually decreased in the direction from the first contact surface to the second contact surface. The synovial fluid passages disposed in such a manner may ensure that the elasticity of the side, close to the first contact surface, of the elastic matrix relatively high and the elasticity of the side close to the second contact surface is relatively low to facilitate contact between the first contact surface and the femoral condyle.

Figure 4:
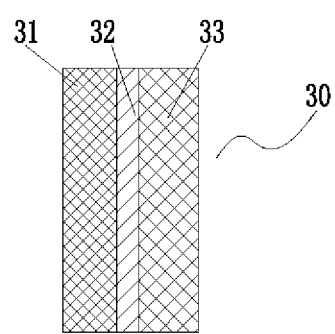
FIG. 4 is a structure diagram of a reinforcing ring of the articular gasket prosthesis in FIG. 1 in an A direction.
Figure 5:
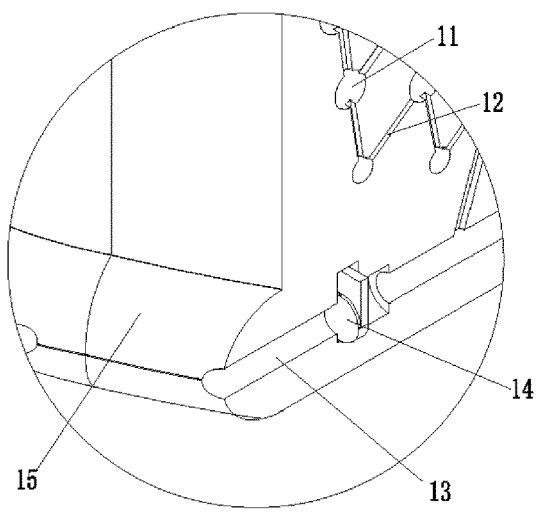
FIG. 5 is a partial enlarged view of the articular gasket prosthesis in FIG. 1 at B.
Figure 6:
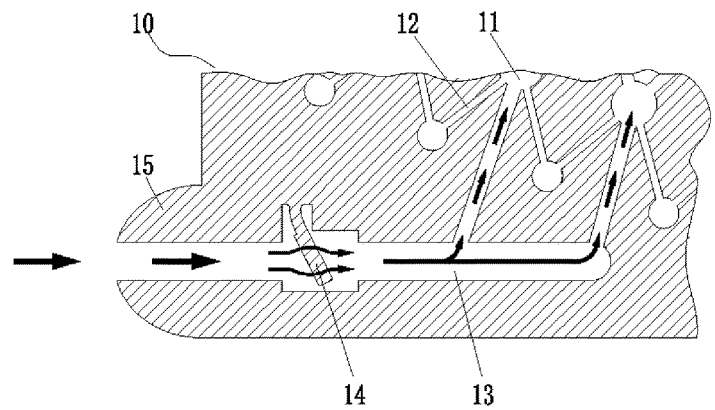
FIG. 6 and FIG. 7 are schematic diagrams of a fluid delivery principle of the articular gasket prosthesis in FIG. 1.
Figure 7:
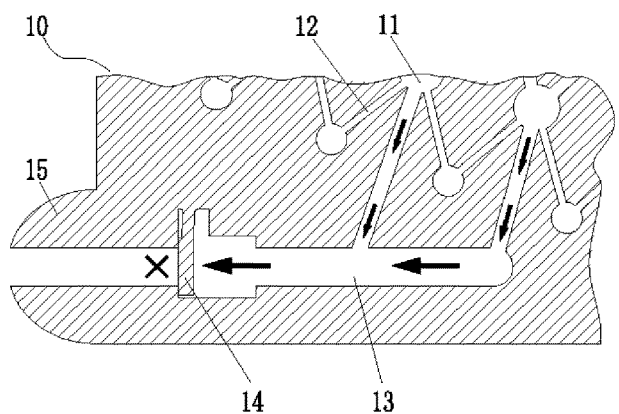

As shown in FIG. 3 to FIG. 7, in the embodiment, the synovial fluid passages further include an inflow passage 13, and the inflow passage 13 is communicated with the accommodation cavities 11 such that the inflow passage 13 is communicated with each accommodation cavity 11 in each accommodation cavity layer and the flow passages 12 connected between each accommodation cavity layer. Furthermore, as shown in FIG. 6 and FIG. 7, a check valve 14 is disposed in the inflow passage 13. As shown in FIG. 7, when the elastic gasket 10 is extruded and deformed by a load, the check valve 14 is closed under backpressure of the synovial fluid, and in such case, the synovial fluid may only be discharged upwards to the first contact surface through the accommodation cavities 11 and the flow passages 12, so that friction between the first contact surface and the femoral condyle is reduced. As shown in FIG. 6, when the load on the elastic gasket 10 disappears, the elastic matrix is restored, negative pressure is formed in the synovial fluid passages, the check valve 14 is opened, and the synovial fluid may enter the accommodation cavities 11 and the flow passages 12 through the inflow passage 13. Therefore, the synovial fluid may be cyclically supplemented and injected to a friction surface during knee joint motions.

As shown in FIG. 1 to FIG. 3, the articular gasket prosthesis of the embodiment further includes a gasket matrix 20, the gasket matrix 20 is disposed between the femur structure and the tibia structure, the gasket matrix 20 is provided with an accommodation groove 21, the elastic matrix 10 is disposed in the accommodation groove 21, and a hardness of the gasket matrix 20 is higher than a hardness of the elastic gasket 10. An optional material matching material is that the elastic gasket 10 is made from a polyurethane material, the gasket matrix 20 is made from ultra-high molecular weight polyethylene and may function approximately as a physiological meniscus at an annular edge of the accommodation groove 21 to enhance a support effect and wear resistance of the elastic gasket 10. Structures such as the synovial fluid passages in the elastic matrix 10 may be engraved and ablated from the transparent polyurethane material by use of a femtosecond laser technology.

As shown in FIG. 3, in the embodiment, the gasket matrix 20 further includes a communicating passage 28, an inlet of the communicating passage 28 extends onto a top surface of the gasket matrix 20, and an outlet of the communicating passage 28 is communicated with the inflow passage 13 to guide the synovial fluid into the synovial fluid passages.

In order to fix the elastic gasket 10, as shown in FIG. 1 and FIG. 5, a positioning protruding portion 15 is disposed on a circumferential sidewall of the elastic matrix in the embodiment, and a positioning groove 25 is formed at the position, corresponding to the positioning protruding portion 15, of the accommodation groove 21. After the elastic gasket 10 is placed in the accommodation groove 21, the positioning protruding portion 15 may extend into the positioning groove 25 to prevent the elastic matrix 10 from being separated.

As shown in FIG. 1, the gasket matrix 20 further includes a patellar groove 29 adapted to a patella and a ligament thereof.

As shown in FIG. 1 and FIG. 4, the articular gasket prosthesis of the embodiment further includes a reinforcing ring 30, and the reinforcing ring 30 is disposed in a reinforcing ring accommodation groove 23 on a circumferential outer side of the gasket matrix 20 and preferably made from a medical metallic material. The reinforcing ring 30 is embedded into the circumferential outer side of the gasket matrix 20 to improve bonding strength of the articular gasket prosthesis. Specifically, the reinforcing ring 30 in the embodiment includes a penetration layer 33, an isolation layer 32 and an integration layer 31, and both of the penetration layer 33 and the integration layer 31 are of a porous structure. Preferably, in the embodiment, a pore diameter of the penetration layer 33 of the reinforcing ring 30 is 500 μm to 3,000 μm, and a pore diameter of the integration layer 31 is 400 μm to 2,000 μm. In a molding process, the ultra-high molecular weight polyethylene material for the gasket matrix 20 may penetrate the porous structure of the penetration layer 33 and form contact fusion with the gasket matrix 20 to implement fixed connection between the reinforcing ring 30 and the gasket matrix 20. The integration layer 31 is exposed, ligaments and soft tissues at corresponding parts of the knee joint around the articular gasket prosthesis may grow in pores of the integration layer 31 to form biological tissue integration after the operation, and such biological integration enables the gasket of the tibial plateau and the soft tissues around the joint to form a stable soft tissue system similar to a normal human physiological knee joint, thereby enhancing stability of the implanted knee joint prosthesis. The isolation layer 32 is of a physical structure, and is disposed between the penetration layer 33 and the integration layer 31 to prevent the molten polyethylene from penetrating the integration layer 31 on the outer side in a making process. In a postoperative healing process, the soft tissues such as the ligaments may grow in the pores of the porous structure, and thus the postoperative knee joint system may be more stable.

In the embodiment, the elastic gasket 10 may also be independently disposed between two skeletons forming the joint to realize certain buffering and wear reduction functions and also achieve an effect of enlarging contact areas with the skeletons.

Figure 13:
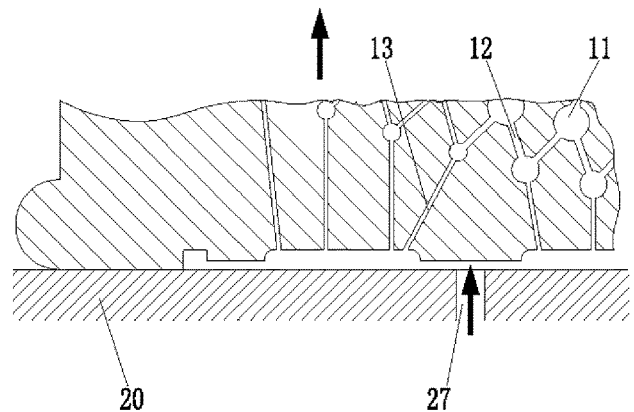
FIG. 13 and FIG. 14 are schematic diagrams of a fluid delivery principle of the articular gasket prosthesis in FIG. 8.
Figure 14:
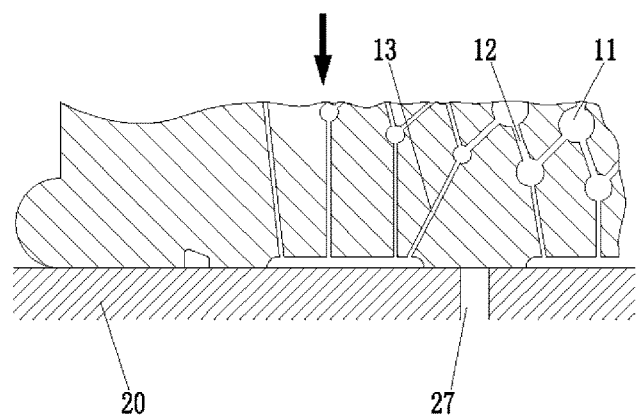

For the articular gasket prosthesis of embodiment 2, an arrangement manner and an inflow manner of the synovial fluid passages are mainly changed on the basis of embodiment 1. As shown in FIG. 8 to FIG. 15, in the elastic gasket 10 of embodiment 2, a synovial fluid accommodation groove is formed in a lower surface of the elastic matrix, and an opening of the inflow passage 13 is disposed at a groove bottom of the synovial fluid accommodation groove. As shown in FIG. 14, when the elastic gasket 10 is extruded by a load, a closed space is formed between the synovial fluid accommodation groove and the gasket matrix 20, and the synovial fluid may be discharged upwards to the first contact surface through the accommodation cavities 11 and the flow passages 12, so that friction between the first contact surface and the femoral condyle is reduced. As shown in FIG. 13, when the load on the elastic gasket 10 disappears, the elastic matrix is recovered, the synovial fluid accommodation groove is separated from the gasket matrix 20, negative pressure is formed in the synovial fluid passages, and the synovial fluid may enter the accommodation cavities 11 and the flow passages 12 through the inflow passage 13. Therefore, the synovial fluid may be cyclically supplemented and injected to the friction surface during knee joint motions.

Figure 15:
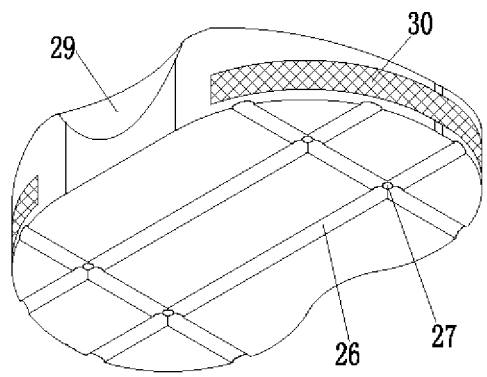
FIG. 15 is a structure diagram of a bottom of a gasket matrix of the articular gasket prosthesis in FIG. 8.
Figure 16:
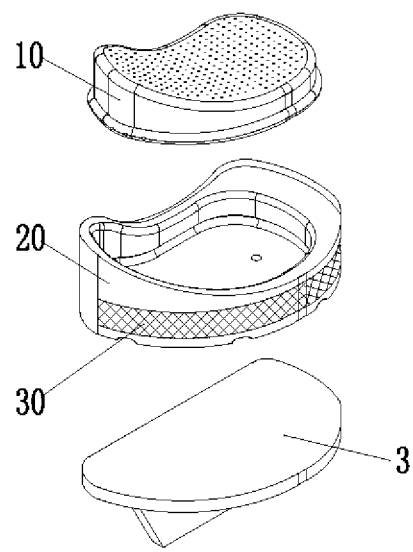
FIG. 16 is an exploded view of an articular gasket prosthesis according to embodiment 3 of the disclosure.
Figure 17:
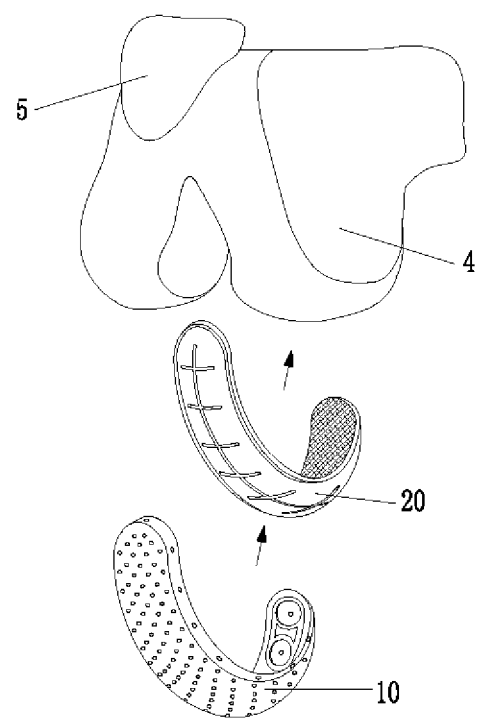
FIG. 17 is an exploded view of an articular gasket prosthesis according to embodiment 4 of the disclosure.

As shown in FIG. 15, in the embodiment, flow grooves 26 are formed in a bottom surface of the gasket matrix 20, and communicating holes 27 are formed in a bottom of the accommodation groove 21 and communicated with the flow grooves 26 such that the synovial fluid may enter the accommodation groove 21 through the flow grooves 26 and the communicating holes 27.

Preferably, in the embodiment, the volumes of the multiple accommodation cavities 11 in the same accommodation cavity layer are gradually decreased from the center to the edge such as an elasticity and hardness distribution of the elastic gasket 10 is closer to primary cartilage tissues of a human body.

The articular gasket prostheses of embodiment 1 and embodiment 2 are applied to a bicondylar knee joint replacement operation. An articular gasket prosthesis of embodiment 3 is applied to a unicompartmental knee joint replacement operation, and an overall structure thereof is approximate to those of the articular gasket prostheses of embodiment 1 and embodiment 2 and will not be elaborated herein.

An articular gasket prosthesis of embodiment 4 is a femoral condyle substitute, and is applied to the unicompartmental knee joint replacement operation. The gasket matrix 20 is disposed on the femoral condyle 4, and the elastic gasket 10 is disposed on the gasket matrix 20.

The application also provides an articular prosthesis. As shown in FIG. 9 to FIG. 11, the articular prosthesis of the embodiment is a knee joint prosthesis, and includes an articular gasket prosthesis 2, a tibial plateau prosthesis 3 and a femoral condyle prosthesis 1. Herein, the articular gasket prosthesis 2 is an articular gasket prosthesis including part or all of the abovementioned technical features. The articular prosthesis of the embodiment has the advantages of relatively low pressure between contact surfaces and long service life.

It can be understood that the technical concept of the embodiment may also be applied to other joint structures such as a shoulder joint and a hip joint.

From the above description, it can be seen that the abovementioned embodiments of the disclosure have the following technical effects.

The synovial fluid passages are disposed in the elastic gasket according to the predetermined manner, and parameters such as sectional shapes, pore diameters, lengths, volumes, positions and arrangement direction and density of the synovial fluid passages are regulated to gradually increase the hardness of the elastic matrix from the center to the edge and gradually decrease the elasticity from the center to the edge, so that different elasticity and hardness indexes may be achieved at different predetermined parts of the elastic gasket to make the elastic gasket close to mechanical characteristics of a human joint as much as possible, the elastic gasket may fully contact with an articular skeleton during joint motions, pressure between contact surfaces is further kept within an ideal range, and a using effect and service life of the articular gasket prosthesis are ensured.

The above is only the preferred embodiment of the disclosure and not intended to limit the disclosure. For those skilled in the art, the disclosure may have various modifications and variations. Any modifications, equivalent replacements, improvements and the like made within the spirit and principle of the disclosure shall fall within the scope of protection of the disclosure.

What is claimed is:

1. An articular gasket prosthesis, comprising an elastic gasket disposed between a first skeleton and a second skeleton, wherein the first skeleton and the second skeleton form a joint, the elastic gasket comprising:
   an elastic matrix, being provided with a first contact surface facing the first skeleton and a second contact surface facing the second skeleton; and
   a plurality of synovial fluid passages, distributed in the elastic matrix and communicating with the first contact surface and the second contact surface, the plurality of synovial fluid passages being disposed according to a predetermined manner, so as to gradually increase a hardness of the elastic matrix from a center to an edge and gradually decrease an elasticity of the elastic matrix from the center to the edge;
   wherein the plurality of synovial fluid passages comprise a plurality of accommodation cavity layers and a plurality of flow passages, the plurality of accommodation cavity layers are disposed in a direction from the first contact surface to the second contact surface, each of the plurality of accommodation cavity layers comprises a plurality of accommodation cavities, and each of the plurality of flow passages is connected between two adjacent accommodation cavities of the plurality of accommodation cavities;
   wherein the plurality of synovial fluid passages further comprise an inflow passage, and a check valve is disposed in the inflow passage, the inflow passage is communicated with at least one accommodation cavity of the plurality of accommodation cavities, or the inflow passage is communicated with at least one flow passage of the plurality of flow passages, or the inflow passage is communicated with at least one accommodation cavity of the plurality of accommodation cavities and at least one flow passage of the plurality of flow passages.

2. The articular gasket prosthesis as claimed in claim 1, wherein volumes of the plurality of accommodation cavity layers are gradually decreased in the direction from the first contact surface to the second contact surface.

3. The articular gasket prosthesis as claimed in claim 2, wherein volumes of the plurality of accommodation cavities are gradually reduced in the direction from the first contact surface to the second contact surface.

4. The articular gasket prosthesis as claimed in claim 1, wherein volumes of the plurality of accommodation cavities in a same accommodation cavity layer are gradually decreased from a center to an edge of the same accommodation cavity layer.

5. The articular gasket prosthesis as claimed claim 1, further comprising a gasket matrix, wherein the gasket matrix is disposed between the first skeleton and the second skeleton, the gasket matrix is provided with an accommodation groove, the elastic gasket is disposed in the accommodation groove, and a hardness of the gasket matrix is higher than a hardness of the elastic gasket.

6. The articular gasket prosthesis as claimed in claim 5, wherein the articular gasket prosthesis further comprises a positioning protruding portion disposed on a circumferential sidewall of the elastic matrix, and a positioning groove is formed at a position, corresponding to the positioning protruding portion, of the accommodation groove.

7. The articular gasket prosthesis as claimed in claim 5, wherein the articular gasket prosthesis further comprises the articular gasket prosthesis further comprises a flow groove is formed in a bottom surface of the gasket matrix, and a communicating hole is formed in a bottom of the accommodation groove and communicated with the flow groove, such that a synovial fluid is able to enter the accommodation groove through the flow groove and the communicating hole.

8. The articular gasket prosthesis as claimed in claim 5, wherein the gasket matrix further comprises a communicating passage, an inlet of the communicating passage extends onto a top surface of the gasket matrix, and an outlet of the communicating passage is communicated with the inflow passage.

9. The articular gasket prosthesis as claimed in claim 5, further comprising a reinforcing ring, wherein the reinforcing ring is disposed on a circumferential outer side of the gasket matrix.

10. The articular gasket prosthesis as claimed in claim 9, wherein the reinforcing ring comprises a penetration layer, an isolation layer and an integration layer, the penetration layer is able to form contact fusion with the gasket matrix, soft tissues around the joint are able to grow in the integration layer, and the isolation layer is disposed between the penetration layer and the integration layer.

11. The articular gasket prosthesis as claimed in claim 10, wherein both of the penetration layer and the integration layer are of a porous structure, a pore diameter of the porous structure of the penetration layer is 500 μm to 3,000 μm, and a pore diameter of the porous structure of the integration layer is 400 μm to 2,000 μm.

12. The articular gasket prosthesis as claimed in claim 1, wherein the elastic gasket is made from an elastic transparent polymer material or composite material.

13. An articular prosthesis, comprising the articular gasket prosthesis as claimed claim 1.

14. The articular prosthesis as claimed in claim 13, wherein the articular prosthesis is a knee joint prosthesis, and the knee joint prosthesis further comprises a tibial plateau prosthesis and a femoral condyle prosthesis.

15. The articular prosthesis as claimed in claim 13, wherein the plurality of synovial fluid passages comprise a plurality of accommodation cavity layers and a plurality of flow passages, the plurality of accommodation cavity layers are disposed in a direction from the first contact surface to the second contact surface, each of the plurality of accommodation cavity layers comprises a plurality of accommodation cavities, and each of the plurality of flow passages is connected between two adjacent accommodation cavities of the plurality of accommodation cavities.

16. The articular prosthesis as claimed in claim 15, wherein volumes of the plurality of accommodation cavity layers are gradually decreased in the direction from the first contact surface to the second contact surface.

17. The articular prosthesis as claimed in claim 16, wherein volumes of the plurality of accommodation cavities are gradually reduced in the direction from the first contact surface to the second contact surface.

18. The articular prosthesis as claimed in claim 15, wherein volumes of the plurality of accommodation cavities in a same accommodation cavity layer are gradually decreased from a center to an edge of the same accommodation cavity layer.

\* \* \* \* \*